United States Patent [19]

Adams et al.

[11] 3,957,996

[45] May 18, 1976

[54] PHARMACEUTICAL LOCAL ANESTHETIC COMPOSITIONS

[75] Inventors: Herbert J. F. Adams, Westboro; Bertil H. Takman, Worcester, both of Mass.

[73] Assignee: Astra Pharmaceutical Products, Inc., Worcester, Mass.

[22] Filed: June 12, 1973

[21] Appl. No.: 369,147

Related U.S. Application Data

[63] Continuation-in-part of Ser. No. 206,182, Dec. 8, 1971, abandoned, which is a continuation-in-part of Ser. No. 109,942, Jan. 26, 1971, abandoned.

[52] U.S. Cl................................ 424/253; 424/248; 424/258; 424/267; 424/300; 424/308; 424/310; 424/324; 424/326; 424/232
[51] Int. Cl.².......................................... A61K 31/52
[58] Field of Search ............. 424/253, 324, 95, 263

[56] References Cited
UNITED STATES PATENTS
3,812,147   5/1974   Adams et al........................ 424/324

OTHER PUBLICATIONS

Chemical Abstracts, Vol. 68 (1968), p. 76031k.
Chemical Abstracts, Vol. 63 (1965), p. 10471e.
Adriani et al., Annals of Surgery, Vol. 158, No. 4, 1963, pp. 666–671.
Adriani et al., Chem. Abst. Vol. 60, 1964, p. 7353.
Kao, Pharmacological Reviews, Vol. 18 No. 2 June 1966 p. 1039.
The Merck Index, 7th Ed. 1960 p. 405.

*Primary Examiner*—V. D. Turner
*Attorney, Agent, or Firm*—Brumbaugh, Graves, Donohue & Raymond

[57] ABSTRACT

A local anesthetic composition comprising a mixture in a pharmaceutically acceptable carrier of a particular toxin, namely, saxitoxin, and another compound, generally a conventional local anesthetic compound or a similar compound having nerve-blocking properties.

18 Claims, No Drawings

PHARMACEUTICAL LOCAL ANESTHETIC COMPOSITIONS

This application is a continuation-in-part of our copending U.S. application Ser. No. 206,182 filed Dec. 8, 1971, now abandoned which is a continuation-in-part of our application Ser. No. 109,942 filed Jan. 26, 1971, now abandoned.

The present invention relates to a novel local anesthetic composition comprising a mixture of (1) saxitoxin and (2) another compound, generally a conventional local anesthetic compound or a similar compound having nerve-blocking properties, to methods for the preparation of such a composition and to the use thereof for inducing anesthesia.

Toxins from marine sources of extraordinary potency have been known for many years. This application particularly conerns novel uses for saxitoxin.

Saxitoxin is extracted from the Alaska butterclam, Saxidomus giganteus. Other terms by which the substance is known are clam toxin, mussel toxin, and shellfish toxin. The toxin, despite its name, does not originate in the clam or mussel in which it is found. It is believed to come from algae of the genus Gonyaulax from which a toxin identical to saxitoxin has been obtained. However, it is still not certain that this algae is the only source of the toxin in the Alaska butterclam.

The structure of saxitoxin has not been determined with certainty. Its hydrochloride is given the empirical formula $C_{10}H_{15}N_7O_3 \cdot 2HCl$. According to published literature, the toxin most probably has a perhydropurine nucleus in which are incorporated two guanidinium moieties. (J. L. Wong et al., J. Amer. Chem. Soc. 93, 7344 (1974).

In a voltage-clamped giant axon from the squid or lobster, local anesthetics such as procaine and cocaine reduce both inward initial sodium current and outward potassium current. Inward sodium current can be reduced or even obliterated with saxitoxin, while the outward potassium current is totally unaffected.

Saxitoxin has not found any practical use as an anesthetic. While this compound can be used to induce nerve blocks in laboratory animals, the anesthetic dose is slightly below the lethal dose, which precludes, as a practical matter the use of the compound as an anesthetic in its own right.

Quite surprisingly, combinations of saxitoxin with a local anesthetic compound have been found to possses unusual anesthetic properties. This is manifested most significantly in improved longevity of action of combinations of the toxin with local anesthetics. In these combinations, saxitoxin is used in concentrations below that which produces reliable nerve blocks, and well below the toxic level.

Investigation of a wide variety of local anesthetics has shown that the action of the foregoing toxin in increasing longevity of action is general. Local anesthetics may be classified by characteristic chemical type. Within each chemical type there may be unexplained variations of activity. However, in all cases investigated, each member of the groups investigated has behaved similarly when combined with the foregoing toxin. Specific classes of local anesthetics investigated include anesthetic compounds characterized by i. the aminoacylanilide group, such as lidocaine, prilocaine, bupivacaine, mepivacaine and related local anesthetic compounds having various substituents on the ring system or amine nitrogen;

the following three ester types (ii), (iii) and (iv):

ii. the aminoalkyl benzoate group, such as procaine, chloroprocaine, propoxycaine, hexylcaine, tetracaine, cyclomethylcaine, benoxinate, butacaine, proparacaine, and related local anesthetic compounds;
iii. cocaine and related local anesthetic compounds;
iv. the amino carbamate group, such as diperodon and related local anesthetic compounds;
v. the N-phenylamidine group, such as phenacaine and related local anesthetic compounds;
vi. the N-aminoalkyl amide group, such as dibucaine and related local anesthetic compounds;
vii. the aminoketone group, such as falicain, dyclonine and related local anesthetic compounds; and
viii. the aminoether group, such as pramoxine, dimethisoquine, and related local anesthetic compounds.

In each of the foregoing classes of local anesthetic compounds representative members have been enumerated. The experimental data support the conclusion that the observed effect of the toxin tested of unexpectedly extending the duration of action extend to the other known local anesthetic compounds of these groups and to the obvious modifications of the local anesthetic compounds tested. It may also be anticipated in the light of these discoveries that the novel combinations of the present invention will permit the use of concentrations of conventional local anesthetics in concentrations below the concentrations normally employed clinically. Thereby toxic manifestations sometimes observed as side effects can be minimized.

The chemical structures of some of the foregoing compounds are:

lidocaine procaine chloroprocaine propoxycaine 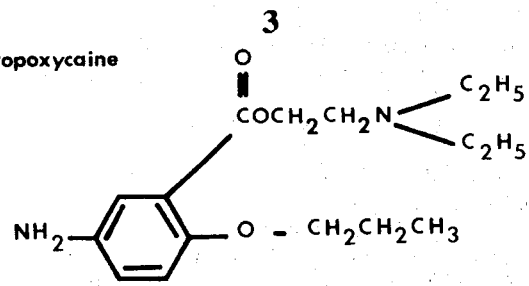
cyclomethycaine 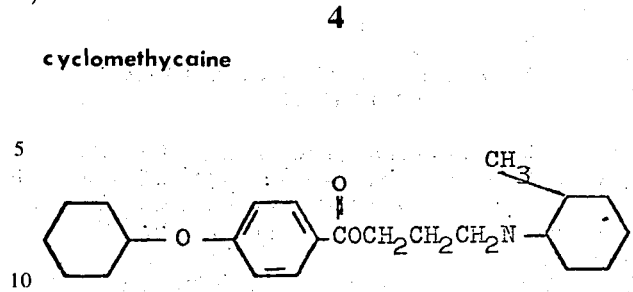
benoxinate 
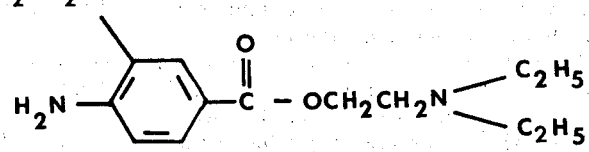
hexylcaine 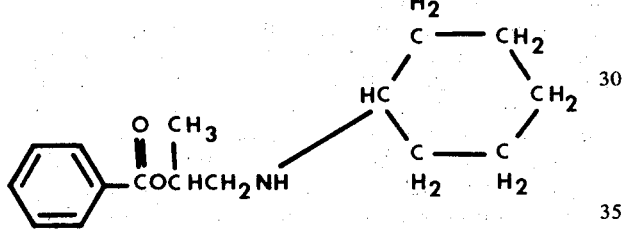
butacaine 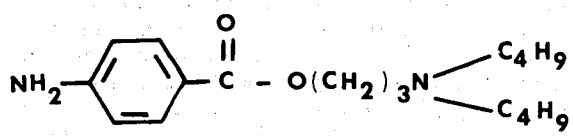
proparacaine 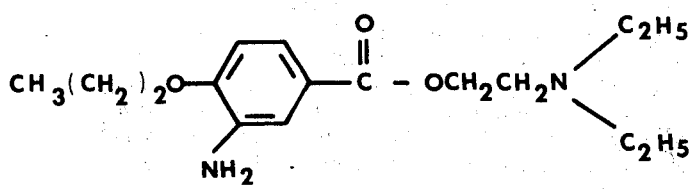
cocaine 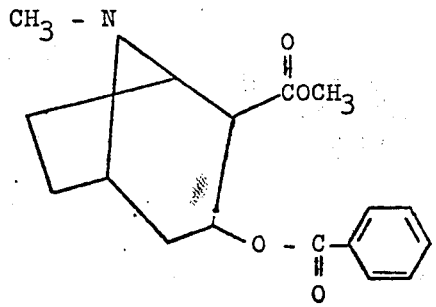
diperodon 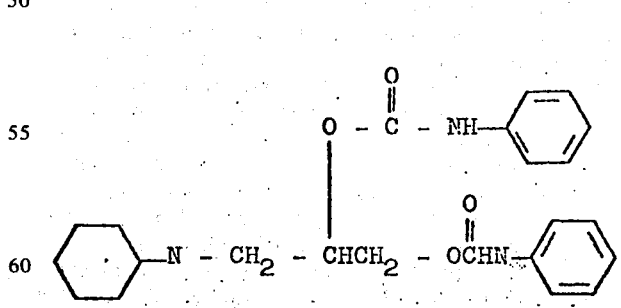
tetracaine 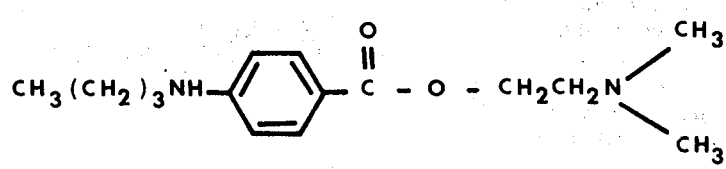

phenacaine $C_2H_5O-\text{C}_6H_4-N(H)-C(CH_3)=N-C_6H_4-OC_2H_5$ dibucaine 2-butoxy-N-(2-diethylaminoethyl)quinoline-4-carboxamide bupivacaine 1-butyl-N-(2,6-dimethylphenyl)piperidine-2-carboxamide mepivacaine 1-methyl-N-(2,6-dimethylphenyl)piperidine-2-carboxamide prilocaine

N-(2-methylphenyl)-2-(propylamino)propanamide falicain $CH_3CH_2CH_2O-C_6H_4-CO-CH_2CH_2-N(\text{piperidinyl})$ pramoxine $CH_3(CH_2)_3O-C_6H_4-O(CH_2)_3-N(\text{morpholinyl})$

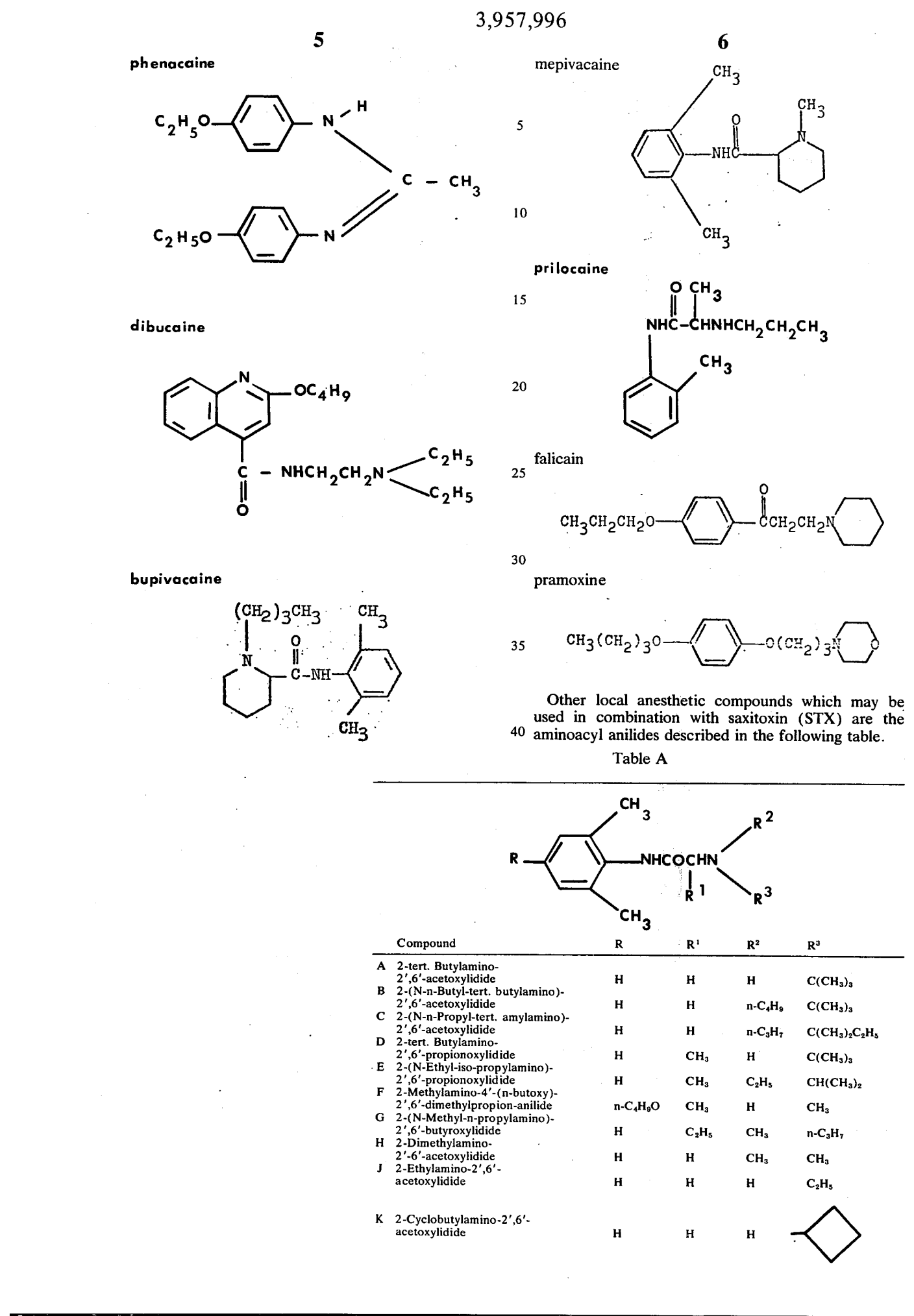

Other local anesthetic compounds which may be used in combination with saxitoxin (STX) are the aminoacyl anilides described in the following table.

Table A

Structure: 2,6-dimethyl-4-R-phenyl-NHCOCH(R¹)N(R²)(R³)

| Compound | | R | R¹ | R² | R³ |
|---|---|---|---|---|---|
| A | 2-tert. Butylamino-2',6'-acetoxylidide | H | H | H | C(CH₃)₃ |
| B | 2-(N-n-Butyl-tert. butylamino)-2',6'-acetoxylidide | H | H | n-C₄H₉ | C(CH₃)₃ |
| C | 2-(N-n-Propyl-tert. amylamino)-2',6'-acetoxylidide | H | H | n-C₃H₇ | C(CH₃)₂C₂H₅ |
| D | 2-tert. Butylamino-2',6'-propionoxylidide | H | CH₃ | H | C(CH₃)₃ |
| E | 2-(N-Ethyl-iso-propylamino)-2',6'-propionoxylidide | H | CH₃ | C₂H₅ | CH(CH₃)₂ |
| F | 2-Methylamino-4'-(n-butoxy)-2',6'-dimethylpropion-anilide | n-C₄H₉O | CH₃ | H | CH₃ |
| G | 2-(N-Methyl-n-propylamino)-2',6'-butyroxylidide | H | C₂H₅ | CH₃ | n-C₃H₇ |
| H | 2-Dimethylamino-2'-6'-acetoxylidide | H | H | CH₃ | CH₃ |
| J | 2-Ethylamino-2',6'-acetoxylidide | H | H | H | C₂H₅ |
| K | 2-Cyclobutylamino-2',6'-acetoxylidide | H | H | H | cyclobutyl |

Note: R, R¹, R², R³ refer to the structure shown with R on the aromatic ring (4-position), R¹ on the α-carbon of the acyl group, and R², R³ on the amino nitrogen, where the parent structure is:

$$\text{R-(2,6-dimethylphenyl)-NHCOCH(R}^1\text{)N(R}^2\text{)(R}^3\text{)}$$

Where applicable, R on the ring shown above appears at the para position (with 2,6-dimethyl groups on the anilide ring).

Table A-continued

[Structure: 2,6-dimethyl phenyl with R substituent, -NHCOCHN(R²)(R³) with R¹ on the CH]

| Compound | R | R¹ | R² | R³ |
|---|---|---|---|---|
| L 2-tert. Amylamino-2',6'-acetoxylidide | H | H | H | C(CH₃)₂C₂H₅ |
| M 2-(N-Methyl-n-butylamino)-2',6'-acetoxylidide | H | H | CH₃ | n-C₄H₉ |
| P 2-(N-Ethyl-sec. butylamino)-2',6'-acetoxylidide | H | H | C₂H₅ | CH(CH₃)C₂H₅ |
| Q 2-Amino-2',6'-propionoxylidide | H | CH₃ | H | H |
| S 2-(N-Ethyl-n-propylamino)-2',6'-butyroxylidide | H | C₂H₅ | C₂H₅ | n-C₃H₇ |
| T 2-Diethylamino-2',6'-valeroxylidide | H | n-C₃H₇ | C₂H₅ | C₂H₅ |

In the present invention the foregoing local anesthetics are used in a pharmaceutically acceptable carrier, such as water, water-ethanol, dextrose solutions, saline solution and blends thereof, in concentrations which are customarily used by physicians. Exemplary concentrations of local anesthetics having clinical application are:

| | % by weight |
|---|---|
| lidocaine | 0.5 – 5 |
| prilocaine | 0.5 – 5 |
| procaine | 0.5 – 5 |
| tetracaine | 0.1 – 1 |
| bupivacaine | 0.25 – 1 |
| hexylcaine | 0.5 – 2.5 |
| compound B | 0.1 – 2.0 |
| compound C | 0.1 – 2.0 |

As mentioned above, the present invention also may permit the use of the usual local anesthetics in a lower-than-normal concentration. For example, the combination of saxitoxin with lidocaine permits the latter to be used in a concentration of as little as 0.05 percent by weight.

The carrier additionally contains from 0.5 to 10, usually from 0.5 to 5, micrograms per milliliter of saxitoxin. In addition, the local anesthetic preparation may contain a vasoconstrictor, as is well known in the art, such as epinephrine, norepinephrine, phenylephrine and levonordefrin.

The local anesthetic compositions may be prepared by dissolving the local anesthetic compound, saxitoxin and a vasoconstrictor, when present, in the carrier or in separate portions of the carrier which are thereafter blended together.

Application of the local anesthetic compositions is accomplished in the usual manner, i.e., by infiltration or injection.

EXAMPLE 1

Female Charles River rats, weighing between 100 and 200 grams, were used. There were 5 rats per group and each animal received 0.2 milliliters of drug solution in the right thigh. The injections were made in such a way as to deposit the solution around the sciatic nerve trunk close to the popliteal space. After being injected, each animal was examined at intervals to determine onset, depth, and duration of nerve block as manifested by impairment of motor function in the injected leg. Frequencies of (a) complete block (b) partial block, and (c) slight effect on motor function were noted for each group of animals. Two end points for duration of block were used: recovery of the ability to grasp when placed on an inclined screen and complete recovery of motor function.

All solutions were freshly prepared on the day of use. None of the solutions contained epinephrine.

The results are summarized in Table I.

TABLE I

| | RAT SCIATIC NERVE BLOCKS | | | | | |
|---|---|---|---|---|---|---|
| Compound | Conc. as Base | pH | Onset (min.) | Frequency C | P | Duration Mean ± Standard Deviation |
| Saxitoxin | 0.5 μg/ml | 5.4 | — | 0/5 | 0/5 | — |
| | 1.0 μg/ml | 5.0 | — | 0/5 | 0/5 | — |
| | 2.0 μg/ml | 4.6 | — | 0/5 | 0/5 | — |
| | 4.0 μg/ml | 4.4 | 14 | 3/5 | 1/5 | 5–20 hours |
| Vehicle (0.08% ethanol in distilled water) | — | — | — | 0/5 | 0/5 | — |
| Saxitoxin | 2.0 μg/ml | 4.8 | 5 | 1/5 | 3/5 | 352 min. |
| Lidocaine | 2.0% | 5.2 | 1 | 5/5 | — | 141 ± 28 min. |
| Saxitoxin ⎤ | 2.0 μg/ml | 4.4 | <1 | 5/5 | — | 6–22 hours |
| Lidocaine ⎦ | 2.0% | | | | | One "blocked" 3 days |

TABLE I-continued

| Compound | Conc. as Base | pH | Onset (min.) | Frequency C | Frequency P | Duration Mean ± Standard Deviation |
|---|---|---|---|---|---|---|
| Dibucaine | 0.125% | 5.6 | 4 | 5/5 | — | 170 ± 33 min. |
| Saxitoxin ⎤ Dibucaine ⎦ | 2.0µg/ml 0.125% | 4.0 | 9 | 5/5 | — | 6–22 hours |
| Procaine | 2.0% | 5.4 | 1 | 5/5 | — | 99 ± 8 min. |
| Saxitoxin ⎤ Procaine ⎦ | 2.0µg/ml 2.0% | 5.4 | 2 | 5/5 | — | 6–22 hours |

Notes: C = Complete block, P = Partial block. Durations are for complete blocks only. Onset times are approximate.

Table I

Saxitoxin, at concentrations of 0.5, 1 and 2 µg/ml, did not produce any blocks in the rat sciatic nerve. At 4 µg/ml it produced block lasting between 5 and 20 hours in 3 out of 5 injected limbs. In combination with lidocaine, procaine, or dibucaine, frequency of block was 100 percent and the blocks lasted between 6 and 22 hours. The saxitoxin-lidocaine combination caused a slight defect in motor function in one leg that persisted for 3 days; however, this animal showed complete recovery of motor function at the end of this time.

EXAMPLE 2

Results of the same test procedure as used in Example 1, but with 1:100,000 epinephrine in all solutions, are set forth in Table II below:

TABLE II

Rat Sciatic Nerve Blocks

| Compound (Conc. as Base) | Onset (min.) | Frequency (%) | Duration* (min.) |
|---|---|---|---|
| Procaine (1%) | 2 | 100 | 104 ± 15 |
| Saxitoxin (1 µg/ml) | — | 0 | 0 |
| Procaine (1%) and Saxitoxin (1 µg/ml) | 2 | 100 | 246 ± 97 |

*Duration times are means ± standard deviation.

EXAMPLE 3

Comparative data on peridural anesthesia in dogs set forth in Table III below was gathered by the following test procedure wherein the volume of injected solution was 5 ml.

Method: Mature male beagles are surgically prepared by implantation of a cannula into a lumbar vertebra so that drug solutions may be administred into the peridural space. After administration of local anesthetic solutions, the animals are examined at intervals for duration of loss of pain in the scrotal area and in the digits of the hind limbs as well as for loss of ability to support their weight.

Response to and awareness of pain stimuli in scrotal areas is a test for anesthetic block in spinal roots L3-4 and S1-2-3. These roots are the furthest removed from the point of injection (L6) and, therefore, least likely to be effected by the anesthetic. Return of response to pain in the scrotum is often the first sign of recovery and indicates recession of anesthesia to at least L4 anteriorly and S2 posteriorly.

In this experiment a dose of saxitoxin that gives no anesthesia of the scrotal area by itself triples the duration obtained with lidocaine by itself.

TABLE III

| PERIDURAL ANESTHESIA IN DOGS | | | | | | |
|---|---|---|---|---|---|---|
| | Onset: Mean and Range | | | Duration: Mean and Range | | |
| Compound and Concentration | Digital Pain | Scrotal Pain | Weight Support | Digital Pain | Scrotal Pain | Weight Support |
| Lidocaine 2% (n=3) | 7<br>5–13 | 8<br>5–13 | 5<br>3–6 | 127<br>72–162 | 111<br>62–152 | 137<br>108–162 |
| Saxitoxin 4μg/ml (n=2) | 19<br>15–23 | No block | 18<br>15–20 | 353<br>307–402 | No block | >7<24** hours |
| Lidocaine 2% Saxitoxin 4μg/ml (n=6) | 5<br>4–6 | 5<br>4–6 | 5<br>4–6 | 426<br>302–556 | 363<br>302–429 | >7<24** hours |

Epinephrine concentration = 1:100,000.
*Onsets and durations are in minutes unless otherwise noted.
For onset times, start of injection was taken as time zero.
n = number of animals.
Salient points:
Lidocaine: frequency good, onset, duration - short
Saxitoxin: duration - long, onset - long, frequency - poor (failure to block scrotal pain)
Combination: frequency, onset and duration better than either component alone.
**>7<24 hours means that the animals were blocked at the end of the day and had recovered the following morning. It is thus not indicating a spread in the duration of action.

The studies on nerve blocking effects on unanesthetized animals of saxitoxin alone and in combination with various local anesthetic agents show that saxitoxin acts to prolong substantially the nerve blocking action of local anesthetic agents but with and without vasoconstrictors.

EXAMPLE 4

The fact that saxitoxin does not increase the general toxicity of local anesthetics is demonstrated in the determination of intravenous toxicity for a mixture of saxitoxin and lidocaine in female albino mice (CRCD strain).

The test method employed for the acute toxicity was as follows:

Sexually mature female animals were used. Animals were divided into groups of 10 and dosed with drug solution or vehicle (isotonic saline). After being dosed, animals were observed at intervals for several hours for overt effects and fatalities. Survivors were housed as groups according to dose level and checked once daily for the duration of the study in order to determine whether or not delayed fatalities occur.

$LD_{50}$'s and 95% Fieller confidence limits (or 95% approximate limits) were calculated by the Minimum Logit Chi Square Method of Berkson, J. Am. Stat. Assoc. 48:565 (1953).

Result:

Lidocaine 1% $LD_{50}$ 26(23–33) mg/kg
Lidocaine 1% + saxitoxin 0.5 µg/ml $LD_{50}$: 27(24–31) mg/kg of lidocaine at a saxitoxin dose of 1.3(1.2–1.6) mg/kg The acute i.v. toxicity of the lidocaine/saxitoxin combination, therefore, appears to be due to the lidocaine, since the $LD_{50}$ for lidocaine in the combination is virtually identical to the $LD_{50}$ for lidocaine by itself.

In similar tests carried out on the female Charles River rats, the toxicity of Compounds B and C of Table A above in combination with saxitoxin was determined subcutaneously. The toxicity of saxitoxin alone was ($LD_{50}$) 11 (9–14) µg/kg. A mixture of a 2% solution of Compound B and 4 µg/ml of saxitoxin had an $LD_{50}$ of 13 (12–23) µg/kg based on saxitoxin. Thus the toxicity based on saxitoxin of the combination was almost identical to the toxicity of saxitoxin alone, proving that there is no potentiation between the toxicities of the two components.

In the same way it was observed that a mixture of a 1% solution of Compound C and 4 µg/ml of saxitoxin had an $LD_{50}$ of 11 (9–15) µg/kg, which again is almost identical to the toxicity of saxitoxin alone. It is concluded, therefore, that there is no potentiation of toxicity as between saxitoxin and either Compound B or C.

Long term studies were carried out on animals to which saxitoxin was administered on a daily basis using a wide range of doses Gross observations were made and outside of the acute $LD_{50}$ range the animals were observed to behave normally and to gain weight in the same manner as the control group.

EXAMPLE 5

Following the method described in Example 1 above, various local anesthetic compounds alone, STX alone and combinations of the compounds with STX were tested for their ability to block the rat sciatic nerve. STX was used uniformly in the amount of 2 µg/ml. No vasoconstrictor was used. The results are presented in Table IV. In the case of compound H in 0.5% concentration duration was about 45 minutes. STX alone produced no anesthesia. In combination, frequency was good and duration was greater than 304 minutes.

In the case of compound J at 1.0% concentration, duration was about 123 minutes, but greater than 420 minutes in combination with STX. In the case of compound K at 1.0% concentration, duration was about 73 minutes, but increased to greater than 420 minutes when combined with STX. For compound L at 0.5% concentration, duration was about 97 minutes alone, whereas in combination with STX duration was greater than 420 minutes. For compound M alone at 1.0% concentration, duration was about 75 minutes but increased to more than 315 minutes in combinatiton with STX. For compound P at 0.5% concentration, duration was only 45 minutes and frequency was poor, whereas in combination with STX duration was about 195 minutes with substantially improved frequency. For compound Q at 0.5% concentration duration was about 44 minutes alone but increased to greater than 420 minutes in combination with STX.

For the known anesthetic falicain at 0.25% concentration duration was about 94 minutes, whereas in combination with STX, duration was up to 420 minutes or more. For the known local anesthetic pramoxine at 0.25% concentration no anesthetic effect whatever was observed, whereas in combination with STX, one complete block of 231 minutes duration was produced.

TABLE IV

Rat Sciatic Nerve Blocks

Saxitoxin (STX) (2 µg/ml) and Various Local Anesthetic Compounds

| Compound and Concn. | | Frequency | Duration (min.) Mean ± S.D. |
|---|---|---|---|
| STX | | 0/6 | 0 |
| H (0.5%) | | 5/6 | 45 ± 1 |
| H (0.5%) | + STX | 5/6 | >304* |
| H (1.0%) | | 6/6 | 76 ± 12 |
| H (1.0%) | + STX | 6/6 | >420 |
| STX | | 0/6 | 0 |
| J (1.0%) | | 6/6 | 123 ± 23 |
| J (1.0%) | + STX | 6/6 | >420** |
| STX | | 0/6 | 0 |
| K (1.0%) | | 6/6 | 73 ± 20 |
| K (1.0%) | + STX | 6/6 | >420 |
| STX | | 0/6 | 0 |
| L (0.5%) | | 6/6 | 97 ± 4 |
| L (0.5%) | + STX | 6/6 | >420 |
| L (1.0%) | | 6/6 | 101 ± 8 |
| L (1.0%) | + STX | 6/6 | >420 |
| STX | | 0/6 | 0 |
| M (1.0%) | | 5/6 | 75 ± 14 |
| M (1.0%) | + STX | 6/6 | >315 |
| STX | | 0/6 | 0 |
| P (0.5%) | | 2/6 | 45 |
| P (0.5%) | + STX | 5/6 | 195 ± 54 |
| STX | | 1/6 | >420 |
| Q (0.5%) | | 4/6 | 44 ± 8 |
| Q (0.5%) | + STX | 5/6 | >420 |
| Q (1.0%) | | 5/6 | 79 ± 19 |
| Q (1.0%) | + STX | 6/6 | >420 |
| STX | | 0/5 | 0 |
| Falicain | (0.25%) | 5/5 | 94 ± 21 |
| Falicain | (0.25%) + STX | 5/5 | 84; 340; >420** |
| STX | | 0/5 | 0 |
| Pramoxine | (0.25%) | 0/5 | 0 |
| Pramoxine | (0.25%) + STX | 1/5 | 231 |

*The symbol > in the column showing duration indicates that the block lasted longer than the time indicated but less than 24 hrs.
**Three animals blocked over 420 min.

EXAMPLE 6

Tests were carried out on the peridural dog according to the procedure described in Example 3 above. Compounds B, C, S and T from Table A above and bupivicaine were tested alone (in most cases) and in combination with STX. Concentrations of local anesthetic compound were from 0.5 to 2%. STX was used uniformly in the concentration of 4 µg/ml. Epinephrine was used as a vasoconstrictor. The results are given in Table V. For the local anesthetics alone, without STX, duration ranged from about 94 minutes in the case of bupivicaine at 0.5%, to 445 minutes in the case of Compound C (at 2%). In combination with STX, durations were substantially longer, that is, up to 1 to 2 days in the case of Compound B + STX (at 2%). All the animals recovered completely and no serious side effects were observed.

TABLE V

| Peridural Anesthesia in Dog | | | |
|---|---|---|---|
| Saxitoxin (STX) (4 μg/ml) and Epinephrine (1:100,000) added to various local anesthetics. Dose Volume: 5 ml unless otherwise noted. | | | |
| Compound and concn. | Number of animals | Duration of block of Digital Pain (min.) | Scrotal Pain (min.) |
| STX | 2 | 307–402* | 0 |
| B (2%) | — | — | — |
| STX + B (2%) | 2 | 1 – 2 days | >420** |
| C (1%) (10 ml) | 2 | 130; 446 | 192; 251 |
| C (2%) | 2 | 104; 575 | 110; 445 |
| STX + C (1%) | 2 | 1 – 2 days | >480 |
| S (0.75%) | 4 | 151 (77–256) | 128 (82–173) |
| STX + S (0.75%) | 2 | 579, >540 | 242, 325 |
| T (1%) | 3 | 301 (238–365) | 202 (185–218) |
| STX + T (1.0%) | 2 | >540 | 489, 403 |
| Bupivicaine (0.5%) | 2 | 232–269 | 94, 139 |
| STX + Bupivicaine (0.5%) | 2 | >600 | 390, 429 |

*Cf. Table III
**The symbol >indicates that the block lasted at least for the period indicated by the number following it but less than 24–48 hrs.

EXAMPLE 7

Compound C of Table A was tested alone and in combination with STX in spinal anesthesia in sheep. The results and the procedure followed are described in Table VI below. It is significant that particularly in the case of digital pain, the addition of Compound C to saxitoxin increased the duration of block from about 69 to about 276, an increase of about 3 ½ fold.

TABLE VI

| Spinal Anesthesia in Sheep with Compound C (0.25%) and Saxitoxin (STX) (3 μg/ml). | | | | |
|---|---|---|---|---|
| Drug | Onset time (min.) | Duration of Block (Min.) Anal. Pain | Vulv.-Scrotal Pain | Digital Pain |
| STX | 3–8 | 172 | 95 | 69 |
| C + STX | 3 | 280 | 265 | 257 |

Method: The solutions contained 7.5% dextrose (pH 4.0). One ml was administered in each experiment. The sheep (23–29 kg) were restrained in the horizontal position during the injection and then immediately tilted so that the slope of the spine was positioned ten degrees to the horizontal plane (caudal inferior). The administration was performed between L6-S1 and was made with 22 gauge three inch disposable needles using the so-called "lateral" rather than the midline approach.
Note: Compound C alone in a concentration of 1%, i.e., four times the concentration used in the experiments summarized above, provided a duration of block of digital pain that lasted for 45–60 min. with an onset time of 5–10 minutes.

Compounds A, B, C, D and L described in Table A above are made by the procedure described in U.S. Pat. application Ser. No. 369,146, filed June 12, 1973, now U.S. Pat. No. 3,925,469 which is a continuation-in-part of Ser. No. 325,378, filed January 22, 1973, now abandoned, both assigned to the same assignee as the present application, which disclosure is incorporated herein by reference.

The method of preparing compounds S and T is disclosed in U.S. Pat. application Ser. No. 164,022 filed July 19, 1971, now U.S. Pat. No. 3,812,147, which is incorporated herein by reference.

The method of preparing compound Q is disclosed in U.S. Pat. application Ser. No. 321,590 filed Jan. 8, 1973, now abandoned, which is incorporated herein by reference.

Compounds H, J and M and mepivacaine are known compounds disclosed in the published literature.

EXAMPLE 8

Synthesis of 2-(N-ethyl-isopropylamino)-2′,6′-propionoxylidide (Compound E)

A mixture of 12.81 g (0.050 mole) of 2-bromo-2′,6′-propionoxylidide, 11.31 g (0.130 mole) ethyl-isopropylamine and 30 ml dry toluene was heated in a glass-lined, stainless-steel pressure vessel at 105° for 20 hours. After cooling to 25°, the brown reaction mixture was filtered, extracted three times with a total of 50 ml of 3 N HCl. The aqueous solution was heated to 75° for ten minutes with decolorizing carbon and then filtered. To the chilled solution was added 10 ml concentrated $NH_3$. The product which precipitated was filtered, washed, and dried. Yield: 6.93 g (52.9%) m.p. 50°–2°.

Anhydrous ethereal HCl was added to 6.90 g of the above base dissolved in 100 ml dry ether until the solution was acidic to moist pH paper, giving 6.15 g of tacky brown material, m.p. 191°–201°. The hydrochloride was recrystallized from a mixture of butanone and alcohol. Yield: 6.02 g, m.p. 207.5°–209°.

Analysis: Calc'd. for $C_{16}H_{27}ClN_2O$: C 64.30, H 9.11, N 9.37, Cl 11.86. Found: C 64.16; H 9.16, N 9.49, Cl 12.09.

EXAMPLE 9

A. Synthesis of 2-Bromo-4′-butoxy-2′,6′-dimethyl propionanilide

To a chilled (ca 10°) solution of 50.7 g (0.263 mole) of 4-butoxy-2,6-dimethylaniline [Buchi et al., Helv. Chim. Acta, 34, 278 (1951)] in 224 ml glacial acetic acid was added rapidly 62.4 g (.289 mole) of 2-bromopropionyl bromide and immediately thereafter a chilled (ca 5°) solution of 87.2 g sodium acetate trihydrate in 362 ml water. This mixture was shaken for ½ hour, filtered, washed with water until the washes were neutral, and dried in vacuo over silica gel and KOH; yield 68.9 g (71.6%); m.p. 132.5°–133.5°. The product was recrystallized from 95% ethanol; m.p. 135.5°–136°.

Analysis: Calc'd for $C_{15}H_2NO_2Br$: C 54.87, H 6.76, Br 24.34. Found: C 55.06, H 6.22, Br 24.69.

B. Synthesis of 2-Methylamino-4′-butoxy-2′,6′-dimethyl-propionanilide (Compound F)

To a cold stirred solution of 14.8 g. of monomethyl amine in 250 ml dry benzene was added (portionwise, keeping temperature below 10°) 19.5 g (0.0594 mole) of 2-bromo-4-butoxy-2′,6′-dimethyl propionanilide (made according to the procedure in the first part of this example); this dissolved readily, forming a clear solution. The mixture was heated to 70° for ca. 1 hr. with stirring, at which point a white precipitate had separated and reflux became so vigorous that the reaction had to be controlled by external cooling.

The precipitated methylammonium bromide was filtered off. Excess amine and solvent were removed in vacuo from the filtrate, giving a white residue which was dissolved in 120 ml 0.5 M HCl and filtered. The filtrate was extracted with 3 × 25 ml. ether; and the ether extracts discarded.

The aqueous phase was alkalized to pH 11, and extracted with ether; the combined extracts were dried ($Na_2SO_4$), filtered, and evaporated, giving a yield of 8.7 g (52.7%); m.p. 107°–107.5°. Recrystallization from cyclohexane did not affect the melting point.

Analysis: Calc'd. For $C_{16}H_{26}N_2O_2$: C 69.0; H 9.41; N 10.06. Found: C 69.0; H 9.17; N 10.06.

EXAMPLE 10

Synthesis of 2-(N-Methyl-n-propylamino)-2',6'-butyroxylidide (Compound G)

To a stirred solution of N-methyl-n-propylamine (9.10 g, 0.125 mole) in 175 ml of anhdyrous benzene was added 2-iodo-butyro-2',6'-xylidide (13.2 g, 0.0415 mole). The mixture was allowed to reflux for 5 hrs.

The reaction mixture was extracted with 1 M HCl. After filtration to remove trace insolubles, the pH was adjusted to 9 with 7 M NaOH, which caused the formation of a light-yellow waxy solid. The latter was filtered, washed with water, and dried; yield 4.00 g (36.7%).

This base was converted to the hydrochloride salt with ethereal HCl. The hydrochloride was twice-recrystallized from ethanol/ether, affording crystals melting at 214°–215°C.

Analysis: Calc'd. for $C_{16}H_{27}ClN_2O$: C 64.3; H 9.11; Cl 11.86. Found: C 64.4; H 9.01; Cl 11.80

EXAMPLE 11

Synthesis of 2-Cyclobutylamino-2',6'-acetoxylidide (Compound K).

To a solution of cyclobutylamine (39.8 g) in 600 ml benzene was added 2-chloro-2',6'-acetoxylidide (49.4 g), slolwy, with stirring, and the mixture was refluxed for about 5 hrs. After cooling, the mixture was filtered to remove the cyclobutylammonium chloride formed. The filtrate was strippd of solvent and excess amine in vacuo; leaving a crude residue.

The residue was dissolved in 0.5 M hydrochloric acid, the solution was made alkaline with sodium hydroxide solution and the base was extracted carefully with ether. The ether solution was dried ($Na_2SO_4$), the ether and low-boiling components were evaporated in vacuo at 40°–50°C and the residue converted to a hydrochloride by addition of ethereal hydrogen chloride to its filtered ether solution. From the hydrochloride the base was obtained by dissolution in water, addition of sodium hydroxide solution to alkaline pH, extraction with ether, drying of the ether extract ($Na_2SO_4$), filtering, and evaporation of the ether. The base could be recrystallized from cyclohexane, petroleum ether (b.p. 60°–110°C), or heptane. The melting point was found to be 75°–78°C.

Analysis: Calc'd. for $C_{14}H_{20}N_2O$: C 72.4, H 8.68, N 12.06. Found: C 72.4, H 8.88, N 11.93.

EXAMPLE 12

A. Synthesis of 2-(sec-butylamino)-2',6'-acetoxylidide

To a solution of 62.2 g of sec-butylamine in 500 ml benzene was added slowly 41.5 g of 2-chloro-2,',6'-acetoxylidide. The mixture was heated to reflux for seven hours and allowed to cool overnight. The precipitate of sec-butyl amine hydrochloride that formed was filtered off and the filtrate was evaporated to an oily residue. The residue was dissolved in ether, and the solution was filtered, dried ($Na_2SO_4$), and evaporated to an oily residue (45.7 g). This crude product was distilled under vacuum, giving an oily liquid that solidified when chilled. Yield: 38.5 g (78%); b.p. 146°/0.05 mm; m.p. 44.5°–45.5°.

Analysis: Calc'd. for $C_{14}H_{22}N_2O$: C 71.75, H 9.46, N 11.96. found: C 71.99, H 9.35, N 12.12. The hydrochloride melted at 176.5°–178.5°.

B. Synthesis of 2-(N-ethyl-sec-butylamino)-2',6'-acetoxylidide (Compound P)

To 140 g of diethyl sulfate was added 30.5 g of 2-(sec-butylamino)-2',6'-acetoxylidide (made by the method described in the first part of this example). The mixture was heated to 100°–110° for five hours and cooled. Water and 5 N HCl were added to pH 2, forming a second phase. After stirring, the aqueous phase (pH 2) was separated, washed with two 100 ml portions of ether and brought up to pH 9 with concentrated $NH_3$. The basic aqueous phase was extracted with five 100 ml portions of ether. The solvent was stripped in vacuo from the combined ether phases, leaving a solidifying oil which was dissolved in ether, dried ($Na_2SO_4$), filtered, and evaporated in vacuo. Yield: 26.2 g (76.8%); m.p. 50.5°–54.5°. The product was twice distilled under high vacuum: b.p. 147°/0.025 mm; 165°10.4 mm. Yield of redistilled product: 21.4 g (62.7%).

Analysis: Calc'd. for $C_{16}H_{26}N_2O$: C 73.23%, H 9.99%, N 10.68%. Found: C 73.06%, H 9.66%, N 10.47%.

We claim:

1. An injectable local anesthetic composition having long-lasting local anesthetic effect which is a solution consisting essentially of a pharmaceutically acceptable carrier having dissolved therein
   a. an aminoacyl anilide local anesthetic compound in a concentration of from 0.05% to 5% by weight of the carrier and
   b. from 0.5 to 10 micrograms of saxitoxin per milliliter of the carrier.

2. The composition as defined in claim 1 wherein the aminoacyl anilide is prilocaine.

3. The composition as defined by claim 1 which further contains an effective amount of a vasoconstrictor.

4. The composition as defined by claim 1 wherein the aminoacyl anilide is 2-(N-ethyl-n-propylamino)-2',6'-butyroxylidide.

5. The composition as defined by claim 1 wherein the aminoacyl anilide is 2-diethylamino-2',6'-valeroxylidide.

6. The composition as defined by claim 1 wherein the aminoacyl anilide is 2-(N-n-butyl-tert.-butylamino)-2',6'-acetoxylidide.

7. The composition as defined by claim 1 wherein the aminoacyl anilide is 2-(N-n-propyl-tert. amylamino)-2',6'-acetoxylidide.

8. The composition as defined by claim 1 wherein the aminoacyl anilide is 2-tert. butylamino-2',6'-acetoxylidide.

9. The composition as defined by claim 1 wherein the aminoacyl anilide is 2-tert. butylamino-2',6'-propionoxylidide.

10. The composition as defined by claim 1 wherein the aminoacyl anilide is 2-dimethylamino-2',6'-acetoxylidide.

11. The composition as defined by claim 1 wherein the aminoacyl anilide is 2-ethylamino-2',6'-acetoxylidide.

12. The composition as defined by claim 1 wherein the aminoacyl anilide is 2-cyclobutylamino-2',6'-acetoxylidide.

13. The composition as defined by claim 1 wherein the aminoacyl anilide is 2-tert. amylamino-2',6'-acetoxylidide.

14. The composition as defined by claim 1 wherein the aminoacyl anilide is 2-(N-methyl-n-butylamino)-2',6'-acetoxylidide.

15. The composition as defined by claim 1 wherein the aminoacyl anilide is 2-(N-ethyl-sec. butylamino)-2',6'-acetoxylidide.

16. An injectable local anesthetic composition having long-lasting local anesthetic effect which is a solution consisting essentially of a pharmaceutically acceptable carrier having dissolved therein
   a. lidocaine in a concentration of from 0.05 to 5% by weight of the carrier and
   b. from 0.5 to 10 micrograms of saxitoxin per milliliter of the carrier.

17. A method of inducing anesthesia in mammals comprising administering to the mammal to be anesthetized an effective amount of an injectable local anesthetic composition having long-lasting local anesthetic effect which is a solution consisting essentially of a pharmaceutically acceptable carrier having dissolved therein
   a. a non-heterocyclic aminoacyl anilide local anesthetic compound in a concentration of from 0.05% to 5% by weight of the carrier, and
   b. from 0.5 to 10 micrograms of saxitoxin per milliliter of the carrier.

18. A method of inducing anesthesia in mammals comprising administering to the mammal to be anesthetized an effective amount of an injectable local anesthetic composition having long-lasting local anesthetic effect which is a solution consisting essentially of a pharmaceutically acceptable carrier having dissolved therein
   a. lidocaine in a concentration of from 0.05 to 5% by weight of the carrier and
   b. from 0.5 to 10 micrograms of saxitoxin per milliliter of the carrier.

* * * * *

UNITED STATES PATENT AND TRADEMARK OFFICE
CERTIFICATE OF CORRECTION

PATENT NO. : 3,957,996
DATED : May 18, 1976
INVENTOR(S) : Herbert J. F. Adams et al It is certified that error appears in the above-identified patent and that said Letters Patent are hereby corrected as shown below:

```
Col. 1, line 35, "(1974)" should read -- (1971) --.  Col. 2,
line 8, "cyclomethylcaine" should read -- cyclomethycaine --.
Col. 10, line 32, "effected" should read -- affected --.  Col.
11, line 43, "doses Gross" should read -- doses.  Gross --.
Col. 13, line 32, the figure "276" should read -- 267 --.
Col. 15, line 31, "slolwy" should read -- slowly --; line 34,
"strippd" should read -- stripped --.  Col. 16, line 41,
"an aminoacyl" should read -- a non-heterocyclic aminoacyl --.
```

Signed and Sealed this

Twenty-first Day of September 1976

[SEAL]

Attest:

RUTH C. MASON
*Attesting Officer*

C. MARSHALL DANN
*Commissioner of Patents and Trademarks*